(12) United States Patent
Li et al.

(10) Patent No.: US 8,729,893 B2
(45) Date of Patent: May 20, 2014

(54) NUCLEAR MAGNETIC RESONANCE 1H AND 13C MULTIPHASE FLOW MEASUREMENTS, ESTIMATING PHASE SELECTED FLOW RATES FROM VELOCITY DISTRIBUTIONS, VOLUME FRACTIONS, AND MEAN VELOCITY

(75) Inventors: Lilong Li, Humble, TX (US); Songhua Chen, Katy, TX (US); Carl M. Edwards, Katy, TX (US); Joo Tim Ong, Houston, TX (US)

(73) Assignee: Baker Hughes Incorporated, Houston, TX (US)

( * ) Notice: Subject to any disclaimer, the term of this patent is extended or adjusted under 35 U.S.C. 154(b) by 362 days.

(21) Appl. No.: 12/907,707

(22) Filed: Oct. 19, 2010

(65) Prior Publication Data

US 2012/0092006 A1 Apr. 19, 2012

(51) Int. Cl.
*G01R 33/563* (2006.01)
*G01N 24/08* (2006.01)
*G01V 3/14* (2006.01)
*G01R 33/44* (2006.01)

(52) U.S. Cl.
CPC ........ *G01R 33/56308* (2013.01); *G01R 33/563* (2013.01); *G01R 33/445* (2013.01); *G01N 24/081* (2013.01); *G01N 24/082* (2013.01); *G01V 3/14* (2013.01)
USPC ............ 324/303; 324/306; 324/307; 324/318

(58) Field of Classification Search
CPC ........... G01R 33/563; G01R 33/56308; G01R 33/445; G01N 24/081; G01N 24/082; G01N 24/08; G01V 3/14
USPC .......................... 324/300–322; 600/407–435; 382/128–131
See application file for complete search history.

(56) References Cited

U.S. PATENT DOCUMENTS

| 4,536,711 | A | | 8/1985 | King et al. |
| 4,574,240 | A | | 3/1986 | Libove et al. |
| 4,609,872 | A | * | 9/1986 | O'Donnell ..................... 324/306 |
| 4,694,253 | A | * | 9/1987 | Le Roux ....................... 324/309 |

(Continued)

FOREIGN PATENT DOCUMENTS

JP 2001269326 10/2001

OTHER PUBLICATIONS

Caprihan et al., "Flow Measurements by NMR," Physics Reports (Review Section of Physics Letters) 198, No. 4, 1990, pp. 195-235.

(Continued)

*Primary Examiner* — Melissa Koval
*Assistant Examiner* — Tiffany Fetzner
(74) *Attorney, Agent, or Firm* — Cantor Colburn LLP

(57) ABSTRACT

A method and apparatus for estimating a flow rate of a phase of a multiphase fluid is disclosed. A first velocity distribution is obtained for a first set of nuclei in the fluid from a Nuclear Magnetic Resonance (NMR) signal received for the fluid in response to a first NMR excitation signal. A second velocity distribution is obtained for a second set of nuclei in the fluid from an NMR signal received for the fluid in response to a second NMR excitation signal. A velocity of the phase is estimated from the first velocity distribution and the second velocity distribution. The flow rate of the phase is estimated using the estimated velocity of the phase and an estimated volume fraction of the phase.

14 Claims, 4 Drawing Sheets

(56) References Cited

U.S. PATENT DOCUMENTS

| | | | |
|---|---|---|---|
| 4,780,674 A * | 10/1988 | Breton et al. ............. 324/309 |
| 4,785,245 A | 11/1988 | Lew et al. |
| 4,901,018 A | 2/1990 | Lew |
| RE33,391 E * | 10/1990 | Breton et al. ............. 324/309 |
| 5,532,593 A * | 7/1996 | Maneval et al. ............ 324/306 |
| 6,046,587 A | 4/2000 | King et al. |
| 6,268,726 B1 * | 7/2001 | Prammer et al. ............ 324/303 |
| 6,362,619 B2 * | 3/2002 | Prammer et al. ............ 324/303 |
| 6,452,390 B1 | 9/2002 | Wollin |
| 6,549,007 B1 | 4/2003 | Hills et al. |
| 6,583,621 B2 * | 6/2003 | Prammer et al. ............ 324/303 |
| 6,822,454 B2 | 11/2004 | Peck et al. |
| 6,825,659 B2 * | 11/2004 | Prammer et al. ............ 324/303 |
| 7,126,332 B2 | 10/2006 | Blanz et al. |
| 7,141,978 B2 | 11/2006 | Peck et al. |
| 7,186,971 B2 | 3/2007 | Riley et al. |
| 7,363,161 B2 * | 4/2008 | Georgi et al. ............... 702/7 |
| 7,372,263 B2 * | 5/2008 | Edwards ................... 324/303 |
| 7,459,907 B2 | 12/2008 | Ganesan |
| 7,501,819 B2 | 3/2009 | Ong |
| 7,719,267 B2 | 5/2010 | Pusiol |
| 7,852,074 B2 * | 12/2010 | Edwards ................... 324/303 |
| 7,872,474 B2 * | 1/2011 | Pusiol et al. ............... 324/306 |
| 8,082,015 B2 * | 12/2011 | Yodh et al. ................. 600/310 |
| 8,143,887 B2 * | 3/2012 | Pusiol ...................... 324/306 |
| 2004/0015332 A1 | 1/2004 | Martin et al. |
| 2005/0216196 A1 | 9/2005 | Akkurt et al. |
| 2006/0020403 A1 | 1/2006 | Pusiol |
| 2006/0273788 A1 * | 12/2006 | Georgi et al. ............... 324/303 |
| 2007/0114996 A1 * | 5/2007 | Edwards ................... 324/303 |
| 2007/0164737 A1 | 7/2007 | Pusiol |
| 2008/0120034 A1 * | 5/2008 | Georgi et al. ............... 702/6 |
| 2008/0174309 A1 | 7/2008 | Pusiol et al. |
| 2008/0186024 A1 * | 8/2008 | Edwards ................... 324/303 |
| 2009/0091322 A1 * | 4/2009 | Posse ....................... 324/307 |
| 2010/0264916 A1 * | 10/2010 | Pusiol ...................... 324/306 |
| 2012/0092006 A1 * | 4/2012 | Li et al. .................... 324/306 |
| 2012/0092007 A1 * | 4/2012 | Li et al. .................... 324/306 |
| 2012/0174684 A1 * | 7/2012 | Pusiol ...................... 73/861.08 |

OTHER PUBLICATIONS

Carr et al., "Effects of Diffusion on Free Precession in Nuclear Magnetic Resonance Experiements," Physical Review, vol. 94, No. 3, May 1, 1954, pp. 630-638.

Kruger et al., "Nuclear magnetic resonance (NMR) two-phase mass flow measurements," Flow Meas. Instrum., vol. 7, No. 1, 1996, pp. 25-37.

Meiboom et al., "Modified Spin-Echo Method for Measuring Nuclear Relaxation Times," The Reiew of Scientific Instruments, vol. 29, No. 8, Aug. 1958, pp. 688-691.

International Search Report and The Written Opinion of the International Searching Authority, or the Declaration for International Application No. PCT/US2011/051497.

Australian Government, Patent Examination Report No. 1 dated Oct. 8, 2013 for Patent Application No. 2011318468.

* cited by examiner

NUCLEAR MAGNETIC RESONANCE 1H AND 13C MULTIPHASE FLOW MEASUREMENTS, ESTIMATING PHASE SELECTED FLOW RATES FROM VELOCITY DISTRIBUTIONS, VOLUME FRACTIONS, AND MEAN VELOCITY

BACKGROUND OF THE DISCLOSURE

Multiphase fluid flows are common in pipes used in the transport of hydrocarbons such as for the petroleum industry. Accurate measurement of flow rates and phases of multiphase fluid flows proves to be difficult. The use of Nuclear Magnetic Resonance (NMR) can be used to determine phase constituents in a fluid. The present disclosure therefore provides a method and apparatus for measuring flow rates of a multiphase fluid flow using NMR techniques.

SUMMARY OF THE DISCLOSURE

In one aspect, the present disclosure provides a method of estimating a flow rate of a phase of a multiphase fluid, the method including: obtaining a first velocity distribution for a first set of nuclei in the fluid from a Nuclear Magnetic Resonance (NMR) signal received for the fluid in response to a first NMR excitation signal; obtaining a second velocity distribution for a second set of nuclei in the fluid from an NMR signal received for the fluid in response to a second NMR excitation signal; estimating a velocity of the phase from the first velocity distribution and the second velocity distribution; and estimating the flow rate of the phase using the estimated velocity of the phase and an estimated volume fraction of the phase.

In another aspect, the present disclosure provides an apparatus for estimating a flow rate of a phase of a multiphase fluid. The exemplary apparatus includes a transmitter configured to provide Nuclear Magnetic Resonance (NMR) excitations to the multiphase fluid; a receiver configured to obtain response signals from the fluid in response to the NMR excitations; and a processor configured to: obtain a first velocity distribution for a first set of nuclei in the fluid from a signal received for the fluid in response to a first NMR excitation; obtain a second velocity distribution for a second set of nuclei in the fluid from a signal received for the fluid in response to a second NMR excitation; estimate a velocity of the phase from the first velocity distribution and the second velocity distribution; and estimate the flow rate of the phase using the estimated velocity of the phase and an estimated volume fraction of the phase.

Examples of certain features of the apparatus and method disclosed herein are summarized rather broadly in order that the detailed description thereof that follows may be better understood. There are, of course, additional features of the apparatus and method disclosed hereinafter that will form the subject of the claims.

BRIEF DESCRIPTION OF THE DRAWINGS

For detailed understanding of the present disclosure, references should be made to the following detailed description, taken in conjunction with the accompanying drawings, in which like elements have been given like numerals and wherein.

DETAILED DESCRIPTION OF THE DISCLOSURE

Figure 1:
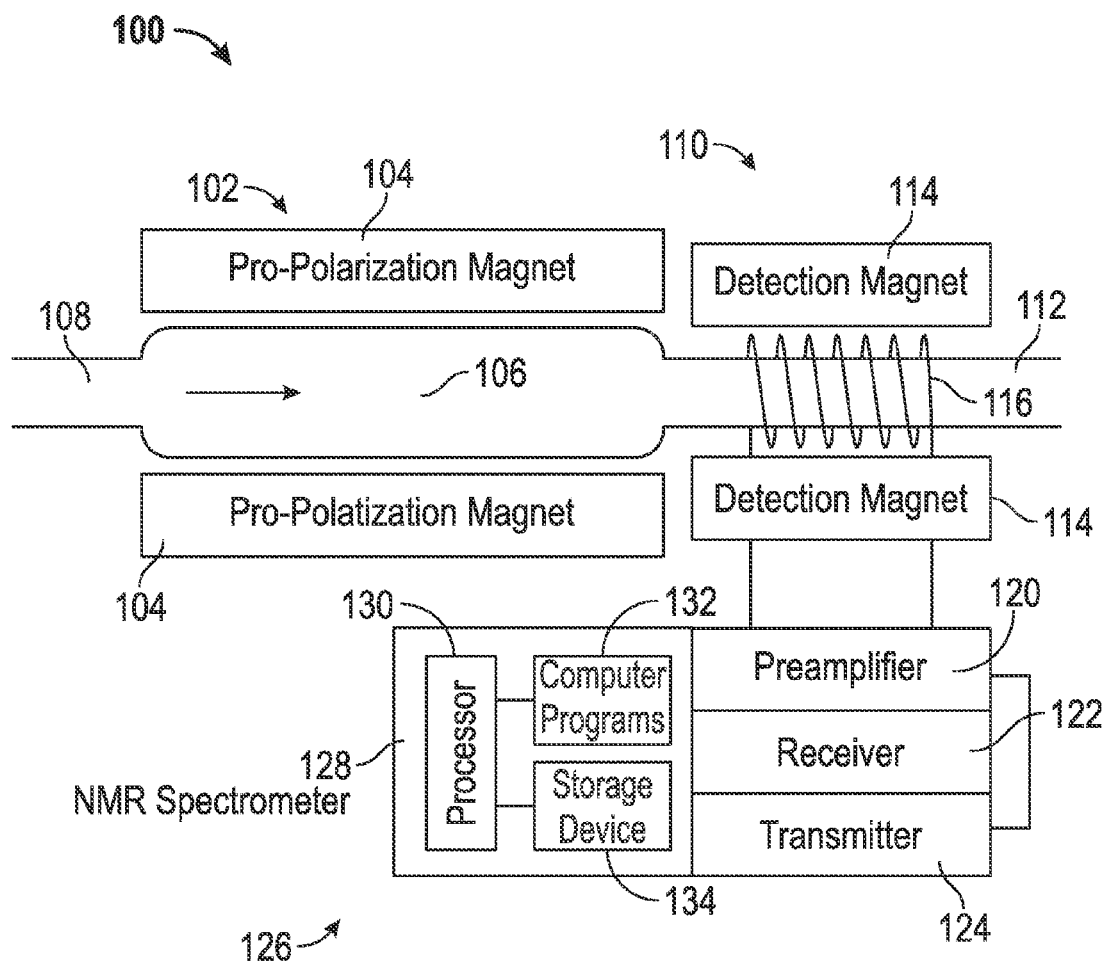
FIG. 1 shows an exemplary Nuclear Magnetic Resonance (NMR) flow meter device for estimating a flow rate of a fluid phase in a pipe using the exemplary methods of the present disclosure.

FIG. 1 shows an exemplary Nuclear Magnetic Resonance (NMR) flow meter device 100 for estimating a flow rate of a fluid phase using the exemplary methods of the present disclosure. In one embodiment, the fluid is a multiphase fluid. In another embodiment, the fluid is a fluid flowing in a production system or a pipe for transportation of hydrocarbons. The exemplary NMR flow meter 100 includes a pre-polarization section 102 for polarizing nuclear spins of fluid along a selected direction, a detection section 110 for providing NMR excitation pulses to the fluid and obtaining NMR signals in response to the NMR excitation pulses from the fluid, and a testing unit 126 for receiving the NMR response signals from the detection section 110 and performing calculations on the received NMR response signals to obtain a flow rate of a phase of the fluid. In the illustrative example of FIG. 1, fluid flows from left to right so as to flow from pre-polarization section 102 into the detection section 110. The pre-polarization section 102 includes a pre-polarization pipe section 106 and a pre-polarization magnet 104 which may be exterior to the pre-polarization pipe section 106 in one embodiment. The pre-polarization magnet 104 is arranged so as to provide a static magnetic field in a volume of the pre-polarization pipe section 106, generally along a substantially axial direction of the pipe section 106. As fluid passes through the static magnetic field, nuclear spins of atoms and molecules within the fluid align along the direction of the static magnetic field. As shown in FIG. 1, the pre-polarization pipe section 106 has a enlarged cross-sectional area. The reason for this particular configuration for the pre-polarization pipe section 106 is discussed below with respect to FIGS. 2A and 2B.

Continuing with FIG. 1, detection section 110 is downstream of the pre-polarization section 102 and receives polarized fluid from the pre-polarization section 102. The detection section 110 includes a detection pipe section 112, a detection magnet 114 which may be exterior to the detection pipe section 112 for providing a static magnetic field in a volume of the detection pipe section 112, and a radio frequency (RF) coil 116. The RF coil 116 encloses a volume within the detection pipe section and is arranged to provide one or more NMR excitation pulses to the fluid in the detection section 110 and to detect one or more NMR response signals from the fluid in the detection section 110.

Testing unit 126 includes various circuitry for obtaining one or more NMR response signals from the fluid and estimating a flow rate of a phase of the fluid from the obtained NMR response signals. The exemplary testing unit 126 is coupled to the RF coil 116 via preamplifier 120. The exemplary testing unit 126 includes a transmitter 124 for providing an NMR excitation pulse to the RF coil 116 via preamplifier 120. In one embodiment, the transmitter 124 provides multiple NMR excitation pulse sequences, each NMR excitation pulse sequence tuned to a selected nuclear resonance frequency. In one aspect, a first nuclear resonance frequency is that of the nuclei of $H^1$ atoms and a second nuclear resonance frequency is that of the nuclei of $C^{13}$ atoms. The exemplary testing unit 126 also includes a receiver 122 for receiving NMR response signals detected at the RF coil 116 via the preamplifier 120. Testing unit 126 also includes an NMR spectrometer 128 for estimating one or more parameters of the fluid from the received NMR response signals using exemplary methods of the present disclosure. In one embodiment, the spectrometer 128 may include a processor 130, one or more computer programs 132 that are accessible to the processor 130 for executing instructions contained in such programs to obtain one or more fluid-related parameters such as a flow rate, and a storage device 134, such as a solid-state memory, tape or hard disc for storing the one or more parameters obtained at the processor 130.

Figure 2A:
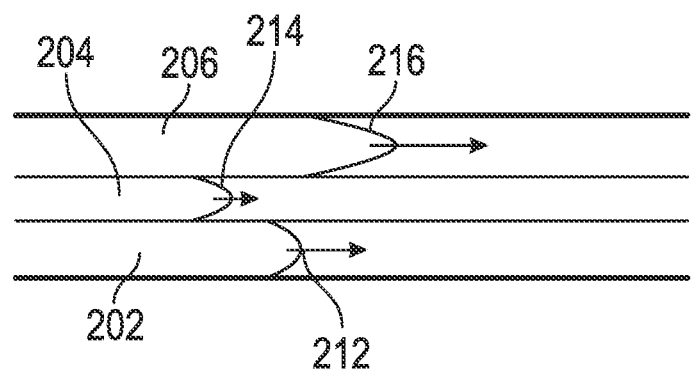
FIG. 2A shows an exemplary multiphase fluid flowing in a pipe.
Figure 2B:
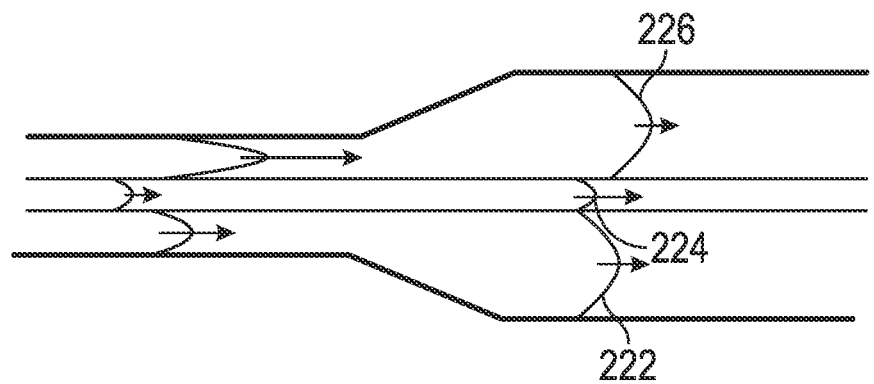
FIG. 2B shows fluid flow of the exemplary multiphase fluid of FIG. 2A in a pipe including a first section having a first radius and a second section having second radius.

The pre-polarization pipe section 106 of FIG. 1 is now discussed in reference to FIGS. 2A and 2B. FIG. 2A shows an exemplary multiphase fluid flowing in a pipe 200. Three phases 202, 204 and 206 of the multiphase fluid are shown. Each phase of the fluid exhibits an exemplary flow velocity profile 212, 214 and 216. A fluid or fluid phase under laminar flow exhibits a velocity profile that has a slow section at the boundaries of the fluid and a fast section typically away from the boundaries. In general, the fast section of the fluid passes through a pipe section before the slowest portion does. The speed of the fluid affects a degree of alignment of the nuclei of the fluid. Nuclear alignment occurs over a characteristic time, as described below with respect to Eq. (1). When a fluid is flowing in a volume of a static magnetic field, the slow portion of the fluid remains in the volume longer than the fast portion of the fluid. Thus, the slow portion of the fluid is typically fully aligned with the static magnetic field upon leaving the volume while the fast portion of the fluid typically leaves the volume without being fully aligned.

FIG. 2B shows fluid flow in a pipe configuration 201 including a first section having a first radius and a second section having a second radius. This pipe configuration of FIG. 2B corresponds in general to upstream pipe section 108 and pre-polarization pipe section 106 of FIG. 1. The radius and therefore the cross-section of the second section is greater than the radius and cross-section of the first section. Flow rate is a volumetric quantity that is a constant proportional to $\pi r^2 \bar{v}$ with $\bar{v}$ being the average velocity. Therefore, the average velocity of the second section (larger cross-section) is less than the average velocity of the first section (smaller cross-section). In addition, flow velocity profiles 222, 224 and 226 are flatter. The maximum velocity $v_m$ of a fluid phase is therefore reduced based on two mechanisms. First, the maximum velocity is reduced due to the reduction of the average velocity. Secondly, the maximum velocity is reduced due to flattening of the flow boundary. Reducing the maximum velocity $v_m$ therefore enables a substantially uniformly polarized fluid to exit the pre-polarization regions, as discussed below.

Reducing maximum velocity also affects design considerations for the length of the pre-polarization magnet. The magnetic polarization $M_P$ of a fluid passing through a polarizing volume such as pre-polarization section 102 is determined by:

$$M_P = M_0(1 - \exp(-t/T_1)) \qquad \text{Eq. (1)}$$

where t is the residence time of the fluid inside the polarizing volume, $T_1$ is a spin-lattice relaxation time, and $M_0$ is the maximum polarization amplitude. For a portion of a fluid that moves with a velocity v and passes through a volume of magnetization length $L_M$, Eq. (1) can be rewritten as $$M_P = M_0(1 - \exp(-L_M/vT_1)) \qquad \text{Eq. (2)}$$

For a general fluid flow, a slow portion of the fluid generally reaches a maximum polarization (degree of alignment), i.e. $M_p \neq M_0$ by the time it exits the pre-polarization volume. The length requirement for a magnet producing a volume to polarize a fast fluid portion is determined by Eq. (2) and the maximum velocity $v_m$ of the fluid through the polarizing volume. Therefore, reducing $v_m$ can reduce the length requirement of the magnet ($L_M$) by a proportional amount.

Methods for obtaining an NMR signal are now discussed. In a typical NMR experiment using the apparatus of FIG. 1, nuclei of various atoms and molecules of a material are subjected to a static magnetic field in the pre-polarization section 102 so that the nuclear spins are aligned along the direction of the static magnetic field as given by Eqs. (1) and (2). When the fluid enters the detection section 110, a radio frequency (RF) pulse sequence is applied to the polarized nuclei. The RF excitation pulse sequence may be any number of excitation pulse sequences known in the art for NMR testing including a Carr-Purcell-Meiboom-Gill (CPMG) pulse sequence. The applied excitation pulse sequence typically re-orients the nuclear spins out of alignment with the applied static magnetic field and allows the unaligned nuclei to relax back into alignment with the static magnetic field. The relaxation of these nuclei back into alignment along the direction of the static magnetic field is characterized by a time constant $T_1$ known as the spin-lattice relaxation rate. The unaligned nuclear spins also typically fall out of phase with each other. The rate of dephasing is characterized by a time constant $T_2$ known as the spin-spin relaxation rate. Both $T_1$ and $T_2$ are characteristic of the particular nucleus. Therefore response signals are typically measured to identify constituents of the material. These methods can be used on solids, liquids and gases.

For fluid flowing in the exemplary flow meter device of FIG. 1, nuclei excited by an excitation pulse leave the detection volume enclosed by RF coil 116 at an average flow velocity $\bar{v}$. The number of excited spins remaining in the volume to contribute to the NMR response signal therefore diminishes with time due to fluid flow. At high fluid velocities, the effect of spin relaxation to the signal is negligible in comparison to the effect of fluid velocity. Therefore, the NMR response signal thus decays over time at a rate that is indicative of flow velocity.

A selected response signal may be related to one or more phases of the fluid. A typical multiphase fluid in petroleum exploration contains a hydrocarbon phase and a water phase. The water phase includes primarily water molecules and therefore primarily hydrogen and oxygen atoms. Thus, the water phase is responsive to an $H^1$ NMR excitation. Since carbon atoms are generally not present in the water phase, the water phase is generally unresponsive to $C^{13}$ NMR excitation. The hydrocarbon phase, on the other hand, includes molecules that are relatively rich in carbon atoms. Thus, the hydrocarbon phase is responsive to $C^{13}$ NMR excitations as well as to $H^1$ NMR excitations. Therefore, $C^{13}$ NMR response signals and $H^1$ NMR response signals may be used to determine water and hydrocarbon phase flow velocities and flow rates, as discussed below.

Figure 3:
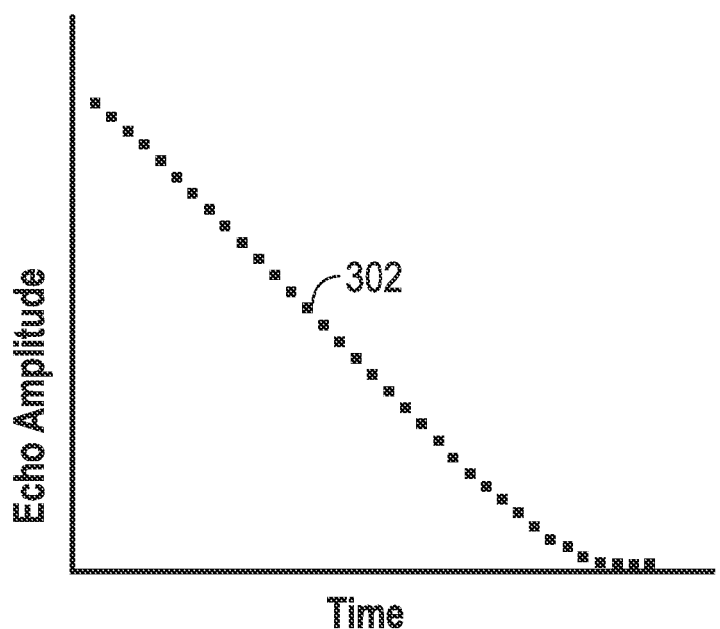
FIG. 3 shows an exemplary signal obtained in response to a NMR excitation pulse applied to a fluid flowing in the exemplary flow meter device of FIG. 1.

FIG. 3 shows an exemplary response signal A(t) measured in response to an NMR pulse as spins pass out of a detection section 110. The exemplary signal of FIG. 3 may represent a response from a particular set of nuclei, such as an $H^1$ response signal or a $C^{13}$ signal. For a particular response signal, the signal may be plotted against time and an extrapolation made to determine an echo signal amplitude at time t=0. A particular response signal obtained at the RF coil 116 has contributions from fluid flowing at various velocities. Thus response signal A(t) can be written as:

$$A(t) = \int_{v=0}^{v_m} a_v \left(1 - \frac{vt}{L_D}\right) \quad v_m = \frac{L_D}{t} \qquad \text{Eq. (6)}$$

where $\alpha_v$ is the signal amplitude of a fluid moving at velocity v and $L_D$ is a length of a detection volume. The majority of the fluid moves at a velocity fast enough so that the majority of the signal decay is due to the moving of excited nuclei out of the volume defined by the RF coil 116, as stated above. Under this condition, Eq. (6) can be rewritten in discrete form:

$$A(t) = \sum_i a_i \left(1 - \frac{v_i t}{L_D}\right) \qquad \text{Eq. (7)}$$

where $\alpha_i$ is the signal amplitude of a fluid moving at velocity $v_i$. Thus, signal amplitude can be determined for a binned value of velocity to obtain a velocity distribution. The velocity distribution may be obtained via any number of inversion methods known in the art.

Figure 4:
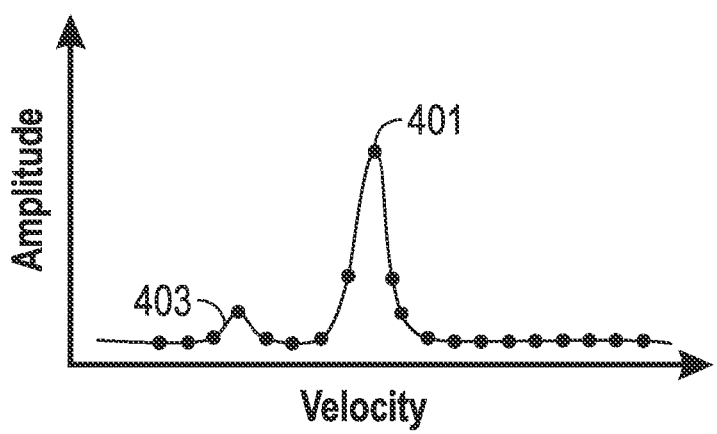
FIG. 4 shows a graph of an exemplary velocity distribution related to the exemplary signal of FIG. 3.

FIG. 4 shows an exemplary velocity distribution 400 relating signal amplitude to velocity for a response signal such as the exemplary response signal of FIG. 3. As an example, FIG. 4 may be a relation between amplitude and velocity for an $H^1$ response signal. A first peak 401 may represent $H^1$ nuclei traveling at a first speed. A second peak 403 may represent $H^1$ nuclei traveling at a second speed. The first and second speeds may be due to flow velocities of different phases, i.e., water and hydrocarbon phases. A flow rate for a particular phase may be estimated using mean velocities obtained from the exemplary velocity distribution such as shown in FIG. 4 and volume fractions obtained from one or more exemplary calibration methods.

In one embodiment, a first NMR excitation pulse is applied to the fluid to excite a first set of nuclei and a first signal is obtained from the first set of nuclei in response to the first excitation pulse. A second NMR excitation pulse is applied to the fluid to excite a second set of nuclei and a second signal is obtained from the second set of nuclei in response to the second excitation pulse. The two signals obtained from the fluid may be used to estimate a flow rate of one or more phases of the fluid, as discussed below.

A flow rate $F_h$ of a hydrocarbon phase flowing through a pipe is given by:

$$F_h = f_h \cdot \bar{v}_h \cdot S \qquad \text{Eq. (3)}$$

where $f_h$ is a volume fraction of the hydrocarbon phase at a specific time, $\bar{v}_h$ is an average velocity of the hydrocarbon phase and S is a cross-sectional area of the pipe. A value of $f_h$ may be determined using various methods. In one embodiment, $f_h$ may be determined from a comparison of a $C^{13}$ NMR response signal from the fluid to a $C^{13}$ NMR signal for a calibrated flow of a hydrocarbon phase in a pipe section having the same configuration as the fluid in the detection pipe section 112.

A total flow rate of a multiphase fluid may be given by:

$$F_T = f_T \cdot \bar{v}_T \cdot S = H_{l,h} F_h + F_W \qquad \text{Eq. (4)}$$

where $F_T$ is the flow rate of the total fluid, $F_W$ is a flow rate of the water phase, $f_T$ is a volume fraction, $\bar{v}_T$ is an average flow velocity of the total fluid as determined from $H^1$ NMR measurements, and $H_{l,h}$ is a hydrogen index of the hydrocarbon phase. Volume fraction $f_T$ may be determined from a comparison of an $H^1$ NMR signal intensity divided by a signal intensity of a water-filled pipe under the same configuration as fluid in the detection pipe section 112. Average flow velocity $\bar{v}T_T$ may be determined from $H^1$ NMR measurements. The ratio of $F_W$ over $F_h+F_W$ provides a water cut of the fluid:

$$S_W = \frac{F_W}{F_h + F_W} \qquad \text{Eq. (5)}$$

A cross-sectional area (i.e., pipe radius) of the detection pipe section 112 may be selected to provide a particular flow velocity. For low velocity flows (i.e., significantly smaller than 1 m/s), the pipe cross-sectional area may be reduced to increase the flow speed and thereby reduce the effects of signal decay on the overall signal. When flow rate varies significantly, a pulsed field gradient module may be added to the NMR instrument to accommodate both high and low flow velocities. At low speed flow, the pulsed field gradient may be used to encode phase changes caused by the flow.

Figure 5:
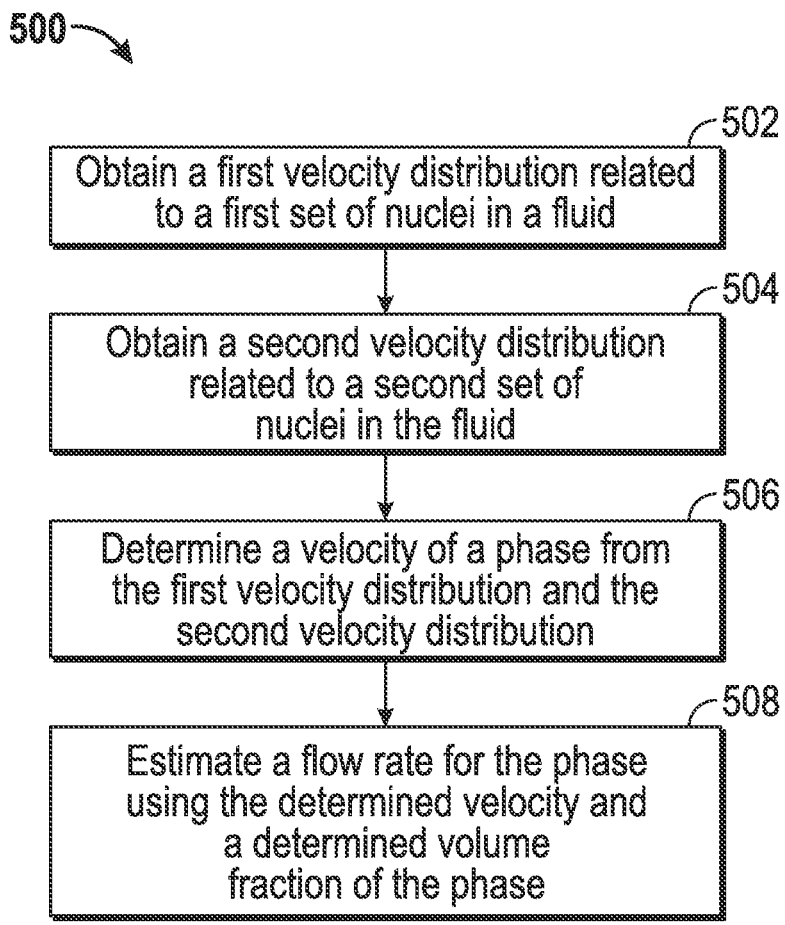
FIG. 5 shows a flowchart of an exemplary method of the present disclosure for determined a flow rate of a phase of a fluid.

FIG. 5 shows a flowchart 500 of an exemplary method of the present disclosure for obtaining a flow rate of a fluid phase. In Box 502, a first velocity distribution is obtained for a first set of nuclei in the fluid. In Box 504, a second velocity distribution is obtained for a second set of nuclei in the fluid. In Box 506, a velocity for a phase of the fluid is determined using the first velocity distribution and the second velocity distribution. In Box 508, a flow rate of the phase is estimated using the determined velocity and a determined volume fraction of the phase.

While the foregoing disclosure is directed to the exemplary embodiments of the disclosure, various modifications will be apparent to those skilled in the art. It is intended that all variations within the scope and spirit of the appended claims be embraced by the foregoing disclosure.

What is claimed is:

1. A method of estimating in the petroleum industry, a flow rate in a pipe, of a selected phase of a multiphase fluid, with an NMR spectrometer comprising:
    obtaining a first velocity distribution of amplitudes from a first set of nuclei in the multiphase fluid from a Nuclear Magnetic Resonance (NMR) signal received from the multiphase fluid in response to a $^1H$ NMR excitation signal;
    obtaining a second velocity distribution of amplitudes from a second set of nuclei in the multiphase fluid from an NMR signal received from the multiphase fluid in response to a $^{13}C$ NMR excitation signal;
    estimating a velocity of the selected phase from the first velocity distribution and the second velocity distribution; and
    in the NMR spectrometer processor:
        determining a volume fraction and a mean velocity of a water phase and a hydrocarbon phase using said amplitudes obtained from the first velocity distribution;
        determining a volume fraction and a mean velocity of the hydrocarbon phase using an amplitude obtained from the second velocity distribution;
        estimating the flow rate of the selected phase, using the determined volume fractions and the estimated velocities, and providing the estimated flow rate of the selected phase to an output storage device of the NMR spectrometer.

2. The method of claim 1, wherein obtaining each velocity distribution further comprises performing inversion on the related NMR signal.

3. The method of claim 1, wherein the multiphase fluid is obtained from an oil field production system.

4. The method of claim 1, wherein estimating a volume fraction of the phase further comprises comparing an amplitude of the obtained NMR signal to a previously determined signal amplitude from a calibrated flow of a hydrocarbon phase in a pipe section having the same configuration.

5. The method of claim 2, wherein further comprising:
aligning the first and second sets of nuclei along a selected direction in a first section of the pipe; and
obtaining the NMR signal in a second section of the pipe.

6. The method of claim 5, further comprising reducing a flow velocity of the phase of the fluid in the first section of the pipe.

7. The method of claim 6, wherein reducing a flow velocity further comprises increasing a radius of the first section of the pipe.

8. An NMR spectrometer apparatus configured for estimating, in the petroleum industry, a flow rate in a pipe, of a selected phase of a multi phase fluid, comprising:
a transmitter configured to provide Nuclear Magnetic Resonance (NMR) excitations to the multiphase fluid;
a receiver configured to receive signals from the multiphase fluid in response to the NMR excitations; and
a processor configured to:
obtain a first velocity distribution of amplitudes from a first set of nuclei in the multiphase fluid from a Nuclear Magnetic Resonance (NMR) signal received from the multiphase fluid in response to a $^1$H NMR excitation signal;
obtain a second velocity distribution of amplitudes from a second set of nuclei in the multiphase fluid from an NMR signal received from the multiphase fluid in response to a $^{13}$C NMR excitation signal;
estimate a velocity of the selected phase from the first velocity distribution and the second velocity distribution;
determine a volume fraction and a mean velocity of a water phase and a hydrocarbon phase using said amplitudes obtained from the first velocity distribution;
determine a volume fraction and a mean velocity of the hydrocarbon phase using an amplitude obtained from the second velocity distribution;
estimate the flow rate of the selected phase, using the determined volume fractions and the estimated velocities, and
provide the estimated flow rate of the selected phase to an output storage device of the NMR spectrometer.

9. The NMR spectrometer apparatus of claim 8, wherein the processor is further configured in order to obtain each velocity distribution by performing an inversion of the correspondingly related response signal.

10. The NMR spectrometer apparatus of claim 8, wherein the multiphase fluid is obtained from an oil field production system.

11. The NMR spectrometer apparatus of claim 8, wherein the processor is further configured to estimate the volume fraction of the selected phase by comparing an amplitude of the received NMR signal to a previously determined signal amplitude from a calibrated flow of a hydrocarbon phase in a pipe section having the same configuration.

12. The NMR spectrometer apparatus of claim 9, further comprising
a polarization magnet configured to align nuclei along a selected direction in a first section of the pipe, and
a coil configured to receive an NMR response sign in a second section of the pipe.

13. The NMR spectrometer apparatus of claim 12, wherein the first section of pipe is configured to reduce a flow velocity of the fluid.

14. The NMR spectrometer apparatus of claim 13, wherein the first section of the pipe has a greater radius than the second section of the pipe.

* * * * *